United States Patent
Rychak

(10) Patent No.: US 9,011,819 B2
(45) Date of Patent: Apr. 21, 2015

(54) OPTICAL IMAGING CONTRAST AGENTS AND USES THEREOF

(75) Inventor: Joshua J. Rychak, La Jolla, CA (US)

(73) Assignee: Targeson, Inc., San Diego, CA (US)

( * ) Notice: Subject to any disclaimer, the term of this patent is extended or adjusted under 35 U.S.C. 154(b) by 147 days.

(21) Appl. No.: 12/888,345

(22) Filed: Sep. 22, 2010

(65) Prior Publication Data

US 2012/0244078 A1    Sep. 27, 2012

Related U.S. Application Data

(60) Provisional application No. 61/277,192, filed on Sep. 22, 2009.

(51) Int. Cl.
*A61B 8/00* (2006.01)
*A61K 49/22* (2006.01)
*A61K 49/00* (2006.01)

(52) U.S. Cl.
CPC ......... *A61K 49/0032* (2013.01); *A61K 49/0002* (2013.01); *A61K 49/0091* (2013.01); *A61K 49/223* (2013.01)

(58) Field of Classification Search
USPC ........................................................ 424/9.52
See application file for complete search history.

(56) References Cited

U.S. PATENT DOCUMENTS

| 5,874,062 | A  | * | 2/1999 | Unger ............................ 424/9.4 |
| 6,123,923 | A  | * | 9/2000 | Unger et al. ................. 424/9.52 |
| 7,329,402 | B2 | * | 2/2008 | Unger et al. ................. 424/9.52 |
| 7,358,226 | B2 | * | 4/2008 | Dayton et al. ................. 514/1.2 |

OTHER PUBLICATIONS

Wikipedia Indocyanine green 2013.*

* cited by examiner

*Primary Examiner* — Michael G Hartley
*Assistant Examiner* — Melissa Perreira
(74) *Attorney, Agent, or Firm* — Kevin S. Helmbacher

(57) ABSTRACT

The present invention generally relates to microbubble contrast agent compositions which are detectable by optical imaging methods, such as fluorescence, near-infrared or bioluminescence. Uses of the described compositions for imaging and therapeutic applications are contemplated.

24 Claims, 11 Drawing Sheets

Figure 1
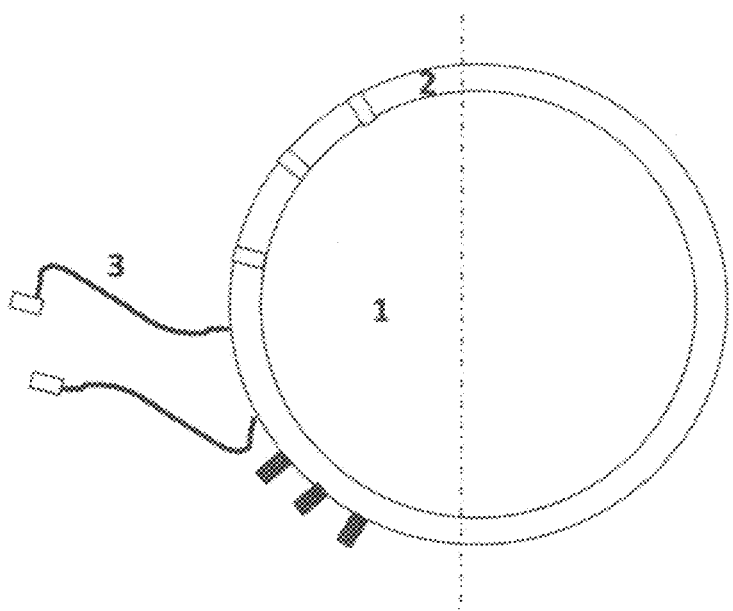
Legend
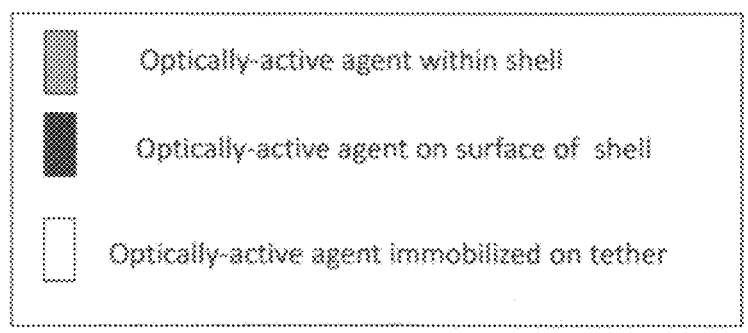

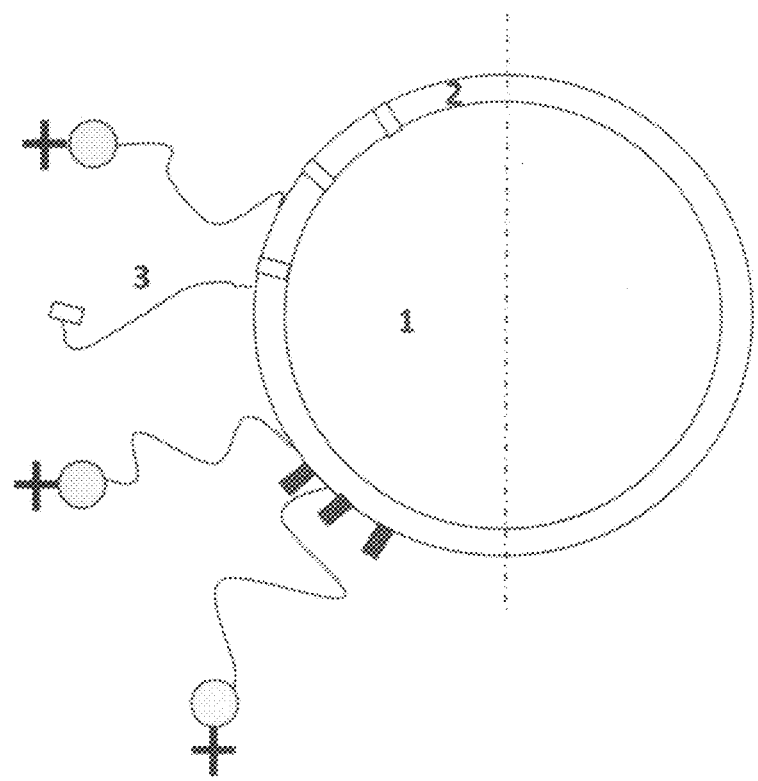
Figure 2
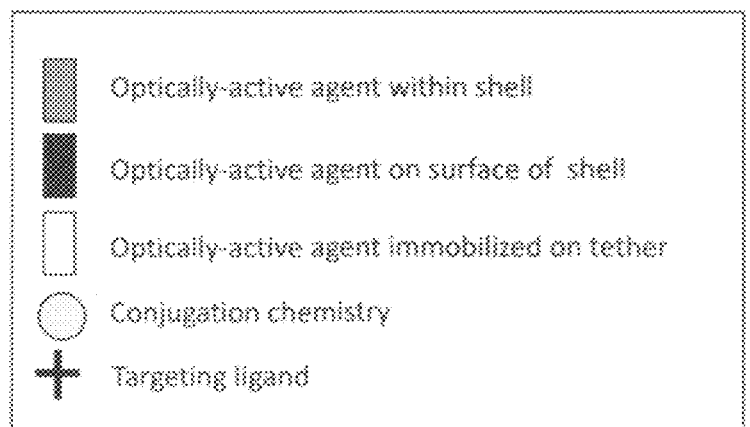
Legend

Figure 3: Derivitization of Microbubbles with Optically Active Reporters

Figure 6
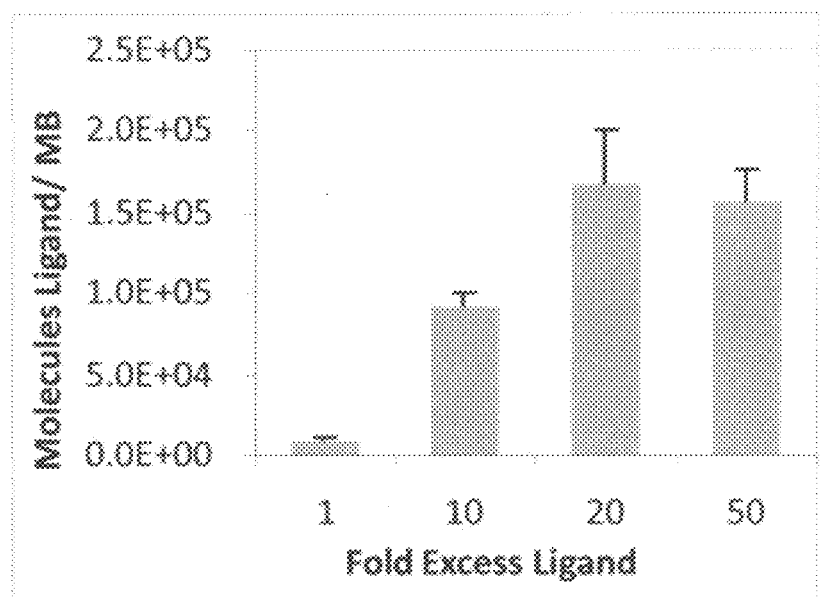
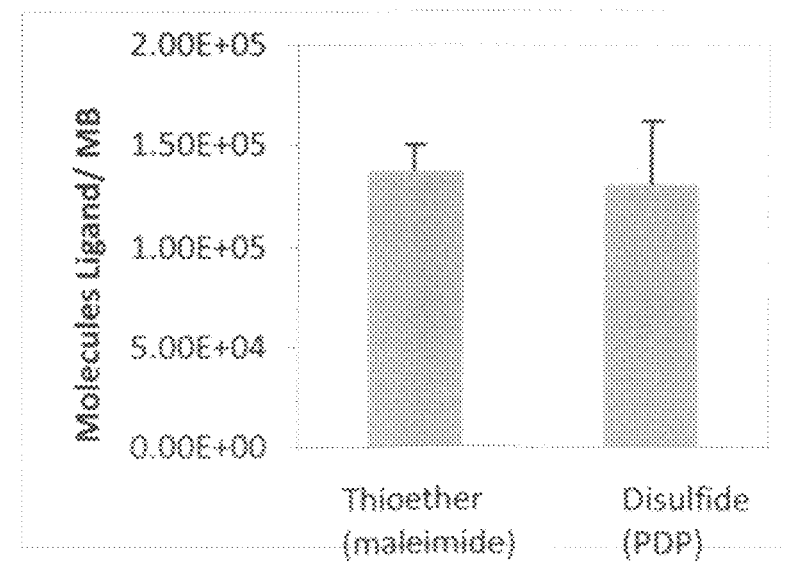

Figure 10
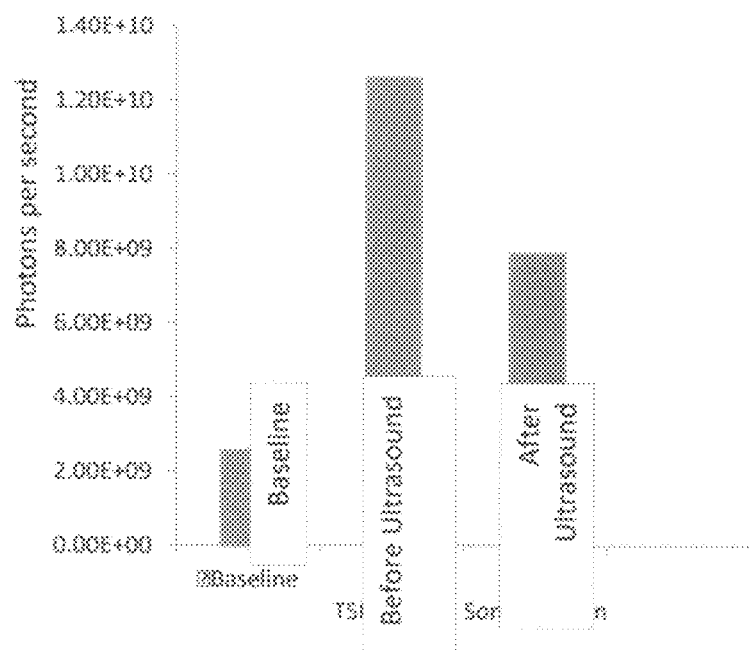
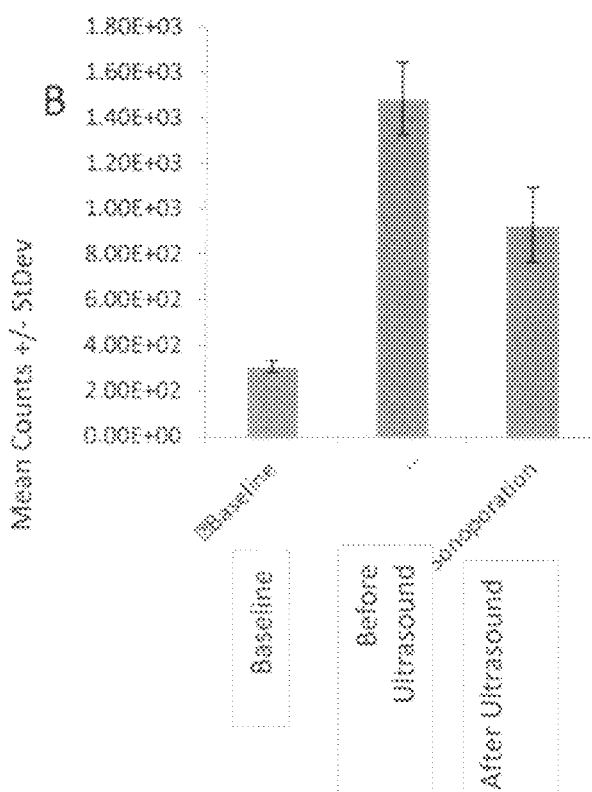

OPTICAL IMAGING CONTRAST AGENTS AND USES THEREOF

CROSS-REFERENCES TO RELATED APPLICATIONS

This application claims the benefit of priority to U.S. Provisional Application No. 61/277,192 filed on Sep. 22, 2009, the contents of which is incorporated herein by reference.

TECHNICAL FIELD

The present invention relates to the field of contrast agents for imaging in the setting of research in vitro and in vivo in animal models, and for diagnostic imaging of veterinary animals and humans. More specifically, the invention relates to microparticle contrast agents that can be used for bioluminescence, fluorescence, and other optical imaging modalities. Use of the described agent for functional imaging (for example, visualizing and measuring blood flow and blood volume) and molecular imaging (for example, visualizing and measuring molecular receptors within the body) are contemplated. Additionally, therapeutic applications are contemplated.

BACKGROUND OF THE INVENTION

Optical imaging is a molecular and functional imaging technique, primarily used for imaging of small animals in a research setting. This technique relies upon sensitive detection of light emitted by luminescent cells, tissues, or contrast agents. Optical imaging can be used to detect certain cell types of interest within the body (for example, cells made to express luciferase for bioluminescence imaging), or to detect contrast agents localized within tissues of interest (for example molecular imaging of a targeted receptor).

Optical imaging using contrast agents typically utilizes molecules or nanoparticles bearing one or more fluorophores, typically active in the near infrared range. Typical contrast agents are injected intravascularly or intraperitoneally, and allowed to accumulate at the target site over several hours to days. A significant difficulty with previously described contrast agents relates to the time required for clearance of unbound contrast. Agents in the nanometer size range can generally distribute throughout the tissues of the body. This can cause a significant non-specific (background) signal, which can require several hours to days to be cleared by the relevant biological pathways; the duration of this clearance is known as the dwell time. A long dwell time can introduce significant inconvenience in imaging workflow, especially in a high-throughput research setting. Additionally, a long dwell period can negate the possibility of administering multiple contrast agent doses within the same imaging setting, due to the requirement that previously administered contrast be fully cleared before subsequent doses can be administered (in order to avoid signal contamination from the previous doses). This can be a problem, for example, in the context of imaging multiple molecular markers within a single patient population. A system whereby contrast agents can be rapidly cleared could significantly benefit molecular imaging workflow.

A second difficulty with previously described contrast agents relates to target specificity. As mentioned above, nanoscale contrast agents distribute throughout the entire body; intravenously administered agents of this size readily diffuse through the vascular wall and into the surrounding tissue due to the very small size of the contrast agent. Many of the molecular imaging targets of key relevance for inflammation, thrombosis, and angiogenesis are expressed on the luminal vascular endothelium or associated cells. Thus, the movement of contrast agents out of the vascular space can introduce off-target non-specific signals. A contrast agent that can be administered intravenously and remain essentially confined to the vascular lumen would enable significantly greater specificity for purely intravascular targets. The present invention overcomes these difficulties.

DEFINITIONS

"Optical Imaging" is defined as the detection and/or measurement of electromagnetic radiation, preferably in the fluorescent or near-infrared region of the spectrum. Said electromagnetic radiation is emitted from the optically active probe. Optical imaging may be accomplished on a cellular level (for example, fluorescence microscopy) or tissue level (for example, small animal imaging).

"Optically Active Probe" is defined as an enzyme, protein, peptide, lipid, nucleic acid, sugar, fluorophore, chromophore, dye, or other chemical capable of emitting electromagnetic radiation. Said electromagnetic radiation can be emitted in response to electromagnetic or acoustic excitation of the optically active probe.

"Targeting ligand" refers to any material or substance that may promote targeting of tissues, cells and/or receptors in vitro or in vivo with the compositions of the present invention. The terms "target(s)", "targeted" and "targeting", as used herein, refer to the ability of targeting ligands and compositions containing them to bind with or be directed towards tissues, cells and/or receptors. The targeting ligand may be synthetic, semi-synthetic, or naturally-occurring. Materials or substances which may serve as targeting ligands include, for example, proteins, including antibodies, glycoproteins and lectins, peptides, polypeptides, saccharides, including mono- and polysaccharides, vitamins, steroids, steroid analogs, hormones, cofactors, bioactive agents, and genetic material, including nucleosides, nucleotides and polynucleotides.

"Target Receptor" or "Molecular Target" refers to a molecular structure within a cell or on the surface of the cell that is generally characterized by the selective binding of a specific substance. Exemplary receptors include, for example, cell-surface receptors for peptide hormones, neurotransmitters, antigens, complement fragments, and immunoglobulins and cytoplasmic receptors for steroid hormones. An exemplary receptor is the vascular endothelial growth factor 2 (VEGFR2), which is frequently associated with angiogenesis.

"Animal Model" is defined as a non-human organism that is used in experimental research. Animal models include but are not limited to mice, rats, frogs, zebra fish, non-human primates, equines, canines, cats, swine, and insects.

"Therapeutic Substance" refers to any therapeutic or prophylactic agent that may be used in the treatment (including the prevention, diagnosis, alleviation, or cure) of a malady, affliction, disease or injury in a patient or animal model. Therapeutically useful peptides, polypeptides and polynucleotides may be included within the meaning of the term therapeutic substance.

"Acoustic Activation" refers to the process of exciting an acoustically active agent, such as a microbubble, with incident acoustic energy. This process may stimulate the agent to produce acoustic energy, which may be detected and quantified by ultrasound imaging. Acoustic activation may further result in the rupture of the agent, whereby the encapsulated gas is released from the shell, and both shell and gas components are removed from the target site by biological means, including incident blood flow. While not intending to be bound by any particular theory of operation, microbubble rupture may occur by deflation of the gas core, explosion, cracking of the shell, or similar processes.

"Acoustically-Activated Delivery" refers to the process of delivering a compound, molecule, nucleic acid, protein, peptide, fluorophore, or reporter into a cell adjacent to a microbubble, wherein both microbubble and cell are treated with a low-frequency (1-10 MHz) high pressure (>50 kPa) acoustic field. While not intending to be bound by any particular theory of operation, acoustically-activated delivery transferring substances into the cell through transient pores or by active transport mechanisms induced by acoustic activation of an adjacent microbubble. Acoustically-activated delivery generally requires the violent destruction of the activated microbubble.

BRIEF SUMMARY OF THE INVENTION

The present invention describes gas-encapsulated microparticles, commonly referred to as a microbubbles, which have been modified to incorporate optically active probes and which can be used as contrast agents for optical imaging. Microbubbles can be produced from various gasses and shells composed of lipid, protein, polymer, or mixtures thereof. The microbubble is inherently echogenic, and is a useful contrast agent for ultrasound imaging.

In one embodiment of the invention, the microbubbles are modified before, during, or after microbubble synthesis in order to incorporate an optically active probe, said probes being detectable by fluorescence, near-infrared, bioluminescence, or other optical imaging methods.

In another aspect of the invention, we describe methods of preparing microbubbles by modifying the microbubbles to incorporate targeting ligands on the outer surface of the microbubble. In one embodiment of the invention, the microbubbles are modified before, during or after microbubble synthesis to incorporate an optically active probe, and also a targeting ligand. In a preferred embodiment, the targeting ligand is a peptide that binds VEGF receptors. In another embodiment of the invention, the optically active probe is incorporated into the shell of the microbubble. In another embodiment of the invention, the optically active probe is immobilized on the surface of the microbubble.

In one embodiment of the invention, the optically active probes can be a light-producing enzyme or a conventional fluorophore, both of which can be detected by optical imaging scanners.

In another embodiment of the invention, we describe methods for manufacturing large quantities of modified microbubbles that are of a quality suitable for pre-clinical or clinical use.

In another aspect of the invention, we describe here a method of using the modified microbubbles to characterize and quantify biological processes in vitro or in vivo in human or veterinary patients, or in animal models of disease. In one embodiment of this invention, microbubbles modified to include an optically active probe and a targeting ligand are administered to a living subject by intravenous, retro-orbital, subcutaneous, intraperitoneal, intra-lymphatic intravascular, oral, intramuscular, intraperitoneal, intralymphatic.subcutaneous, intranasal, intrarectal, interstitial, topically, or intratumoral injection, bolus or infusion. The accumulation of the microbubbles within a target tissue is subsequently detected and/or quantified by optical imaging.

In another aspect of the invention, we describe a method of optical imaging of a subject comprising, administering a microbubble modified to incorporate an optically active probe and a targeting ligand to the subject and thereafter imaging the subject with an optical imaging scanner. After imaging, the microbubbles within the targeted tissue are destroyed by application of low-frequency ultrasound pulses intended to eliminate the microbubbles by outward rectified gas diffusion and subsequent deflation of the microbubble. A second population of microbubbles bearing identical or different optically active probe and identical or different targeting ligands is subsequently administered, and the process is repeated.

In another embodiment of the invention, we describe a method for delivering an optically active probe into one or several targeted cells. Said optically active probe is incorporated into or immobilized onto the shell of the microbubble, in addition to a targeting ligand. Microbubbles maintain proximity with the targeted cell(s) by the bond between the targeting ligand and molecular target on the cell(s). The optically active probe is transferred from the microbubble to the adjacent targeted cells by the process of acoustically-activated delivery. Said acoustic activation should consist of high-amplitude ultrasound of sufficient energy to induce non-linear oscillation and subsequent violent destruction of the microbubble. Cells that receive the optically active probe may be subsequently imaged and quantified using optical imaging.

In another aspect of the invention, we describe therapeutic uses of the described optically active modified microbubbles. In one embodiment of the invention, the therapeutic method comprises, administering a therapeutically effective amount of microbubbles modified by the addition of an optically active probe and a therapeutic substance to a subject, imaging the subject for a period of time during which accumulation of the microbubbles at a desired location in vivo is verified, thereafter rupturing the microbubbles with high-pressure ultrasound in order to release the therapeutic substance. An additional embodiment of this invention involves application of suitable electromagnetic radiation subsequent to ultrasound-mediated microbubble rupture in order to activate the therapeutic agent. In yet another embodiment of this invention, application of electromagnetic radiation occurs prior to ultrasound-mediated microbubble rupture. In one embodiment of the invention, the optically active probe is immobilized on or within the shell of the microbubble. In a preferred embodiment of the invention, the microbubbles are targeted to angiogenic tumor cells by the inclusion of a VEGF targeting ligand.

In another aspect of the invention, we describe therapeutic uses of the described optically active modified microbubbles for delivery of therapeutic substances in vivo. In one embodiment of the invention, the therapeutic method comprises, incubating with the targeted tissue, cells, or medium a therapeutically effective amount of microbubbles modified by the addition of an optically active probe and a therapeutic substance to a subject, imaging the subject for a period of time during which accumulation of the microbubbles at a desired location is verified, thereafter rupturing the microbubbles with high-pressure ultrasound in order to release the therapeutic substance. An additional embodiment of this invention involves application of suitable electromagnetic radiation subsequent to ultrasound-mediated microbubble rupture in order to activate the therapeutic agent. In yet another embodiment of this invention, application of electromagnetic radiation occurs prior to ultrasound-mediated microbubble rupture. In one embodiment of the invention, the optically active probe is immobilized on or within the shell of the microbubble. In another embodiment of this invention, the optically active probe is transferred from the microbubble to the targeted tissue, cells, or medium.

BRIEF DESCRIPTION OF THE DRAWINGS

FIG. 1 is a cross sectional view of the microbubble contrast agents. A gas core (1) is encapsulated by a shell (2). One or more optically active agents can be coupled to the microbubble within the shell, on the surface of the shell, or immobilized on the distal tip of a polymer tether (3).

FIG. 2 illustrates preferred methods of conjugation of ligand to the microbubble surface. A gas core (1) is encapsulated by a shell (2). One or more optically active agents can be coupled to the microbubble within the shell, on the surface of the shell, or immobilized on the distal tip of a tether (3). One or more targeting ligands are immobilized to the microbubble shell via a conjugation chemistry on the distal tip of a polymer tether.

FIG. 6 illustrates the use of targeted microbubbles for optical imaging. (A) Conjugation of a ligand to the microbubble can be optimized by varying reactant concentration; (B) covalent conjugation of ligand via thioether or disulfide bonding under optimized reaction conditions results in equivalent ligand densities on the microbubble surface. The ligand used in these data is scVEGF, as in Example 7.

FIG. 10 illustrates an in vitro demonstration of acoustically-mediated microbubble clearance. Microbubbles containing 3% DiR were placed into an optically and acoustically-transparend cell (OptiCell, Nunc), and the cell was placed flat into the optical imaging scanner (Xenogen IVIS). A baseline scan, consisting of a cell with no microbubbles, was first acquired. Microbubbles were then added to the cell, and a scan was taken. The cell was then exposed to ultrasound energy, as described in Example 14, and the cell was imaged after acoustic treatment. A significant decrease in optical signal was observed after acoustically-mediated microbubble destruction, and was quantified in (A) photons per second and (B) mean photon counts.

DETAILED DESCRIPTION OF THE INVENTION

Figure 3:
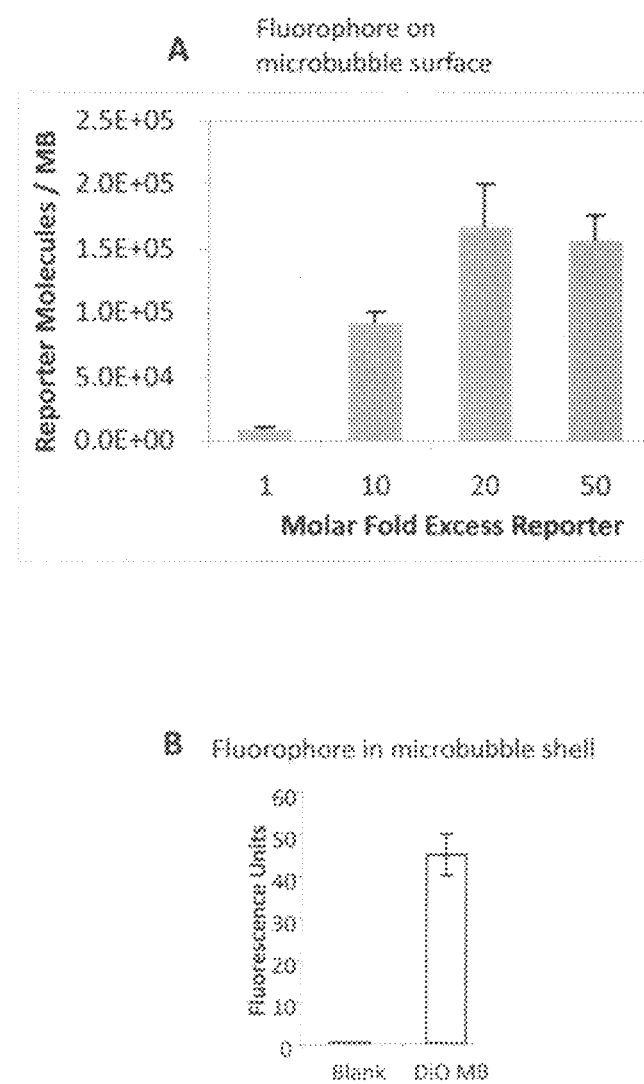
FIG. 3 demonstrates incorporation of fluorescent probes on and within the microbubble shell. (A) Conjugation of a fluorescent reporter on the microbubble surface. BODIPY-Fl-Cystine was incubated at increasing folds excess with maleimide-bearing microbubbles, as in Example 4. Fluorescence corresponding to conjugated fluorophore reporter was assessed using fluorometry. (B) Incorporation of a fluorescent reporter in the microbubble shell. Microbubbles were synthesized with the lipophilic fluorophore DiO as in Example 3. Fluorescent resulting from the reporter incorporated into the shell was quantified by fluorescence spectroscopy using a 96 well plate reader.

This invention describes the construction and use of a microbubble-based contrast agent for optical imaging. The contrast agent contains one or more optically active probes, such as fluorophores or light-generating proteins. The measured optical imaging parameters include transmitted light, absorbed light, fluorescence or phosphorescent emission, reflected light, changes in absorbance amplitude or maxima. For the purpose of imaging in vivo, the use of optically-active probes having activity in the near infrared region (600-1000 nm) are preferred due to the increased penetration in biological tissue relative to light at other wavelengths. Alternatively, bioluminescent proteins, including luciferase, may be used.

The contrast agent consists of a gas-encapsulated microbubble bearing a targeting ligand specific for a molecular target on its surface. The inclusion of the targeting ligand, which may be a peptide, protein, antibody, or other biocompatible molecule, enables the contrast agent to accumulate at sites at which the biological target is located. After administration of the contrast agent into a living subject, the subject is imaged with one or more light sources in the wavelength range suitable for the optically active probe incorporated in the agent. The light used may be monochromatic or polychromatic and continuous or pulsed. Transmitted, scattered, or reflected light is detected via a photodetector tuned to one or multiple wavelengths. Changes in optical parameters may be monitored over time to detect changes in accumulation of the optically-labeled reagent in response to treatment or to monitor disease progression. For example, the targeting ligand may comprise a VEGFR-2-binding antibody, which enables the contrast agent to accumulate at regions of high VEGFR-2 expression within a tumor and thereby monitor the angiogenesis at the molecular level.

The microbubble-based contrast agent is acoustically active. As such, the contrast agent may alternatively be imaged using ultrasound energy in addition to or instead of optical imaging techniques. Methods for imaging microbubble-based contrast agents using ultrasound are well known in the literature. However, the acoustic activity of the microbubble contrast agent, specifically its susceptibility to rupture upon exposure to ultrasound energy, may be alternatively utilized for the purpose increasing imaging efficacy. In this context, the ultrasound-based destruction of the microbubble contrast agent is used to rapidly clear contrast agent from the target site. This enables administration of one or more subsequent contrast agents, for example targeted to another molecular target within the same target tissue. Destruction of the contrast agent upon treatment of the targeted tissue with ultrasound energy enables clearance of the imaging signals from previous doses.

The optical imaging reagents described above may also be used for acousto-optical or sonoluminescent imaging performed with optically-labeled imaging agents. In acousto-optical imaging, ultrasound radiation is applied to the subject and affects the optical parameters of the transmitted, emitted, or reflected light. In sonoluminescent imaging, the applied ultrasound actually generates the light detected.

Microbubbles can be prepared from a variety of gases, including air, nitrogen, argon, sulfur hexafluoride, perfluoroethane, perfluoropropanes, perfluorobutanes, perfluorocyclobutanes, perfluoropentanes, perfluorocyclopentanes, perfluoro methylcyclobutanes, perfluorohexanes, perfluorocyclohexanes, perfluoro methyl cyclopentanes, perfluoro dimethyl cyclopentanes, perfluoro heptanes, perfluoro cycloheptanes, perfluoro cycloheptanes, perfluoromethyl cyclohexanes, perfluoro dimethyl cyclopentanes, perfluoro trimethyl cyclobutanes perfluoro triethylaminesperfluoropropane, perfluorobutane and similar, or a mixture thereof. Microbubbles can be coated with a thin, preferably monolayer, shell of a lipid origin, as well as protein or polymer. Such microbubbles can additionally incorporate a hydrophilic polymer such as polyethyleneglycol (PEG), PVP, or polyglycerol. These substances can act as emulsifiers, increase stability, and assure low non-specific retention of the microbubble to other materials and surfaces. Additionally, microbubbles can be constructed from shells consisting of polymers, proteins, carbohydrates, and combinations of all of the above. Targeting ligands, including antibodies, peptides, lectins, enzymes or other proteins, carbohydrates, vitamins or other molecules, can be attached to the surface of microbubbles using a variety of conjugation chemistries. This enables selective binding of the microbubble to molecular targets of interest. Ligands can be attached to the microbubble shell material directly, via an anchor incorporated into the shell structure, or indirectly via an extended protein or a polymer (for example, PEG) spacer arm. Microbubbles produced by the disclosed methods are generally spherical, with a diameter of between 0.5-15.0 um.

Optically active probes, such as those detectible by fluorescence, near-infrared, and bioluminescence imaging, can be incorporated into or onto the microbubble using a variety of methods disclosed here. Optically active probes are moieties capable of detection by an optical imaging procedure. The optically active probe can be a light scatterer, a light absorber, or light emitter, or a combination thereof. The optically active probe can interact with light at any wavelength. Probes with absorption and emission properties in the near-infrared region are preferred for this invention. Alternatively, the optically active probe can be a photosensitizer.

The optically active probes can be incorporated within or on the microbubble shell. Inclusion of the optically active probes can occur before, during, or after microbubble synthesis. Similarly, conjugation of targeting ligand to the microbubble shell can be performed before, during, or after microbubble formation. Ligand conjugation occurs under appropriate conditions of reactant concentration, pH, ionic strength, temperature, and dissolved gas concentration. Excess ligand and other unreacted components such as lipid and optically active probes may be removed by centrifugal flotation or other methods of separation based upon differences in component density or other physiochemical properties. Microbubbles may be packaged in vials with a headspace of the encapsulated gas (for example, decafluorobutane) and in a buffer saturated with the same gas and generally devoid of air. The stability of targeted microbubbles in storage conditions may be increased by inclusion in the dispersant of excipients, for example PEG, sucrose, trehelose, or other polymers or sugars. Microbubbles may be lyophilized, spray dried, stored intact, or stored as microbubble precursors.

In the invention disclosed here, microbubbles may be synthesized with reactive groups suitable for conjugation of targeting ligands. In one embodiment, a small peptide that binds VEGF receptors, known as scVEGF and described by US No 20050221431, and Backer et al (2007) is utilized as a targeting ligand. Conjugation of other ligands, including antibodies, peptides, carbohydrates, nucleic acids, and other small molecules, can be accomplished using the disclosed methods.

The microbubble agents disclosed here are useful for characterizing and quantifying biological processes in vitro and in vivo using optical and ultrasound imaging, together or separate. Several methods for manufacturing and using the microbubble agents are described. We claim a method of preparing microbubbles bearing optically active probes, and methods for using these agents for molecular imaging in vivo.

We also describe herein a method of delivering an optically active reporter from the microbubble to the targeted cell. This occurs via a process known as acoustically-activated delivery, in which a microbubble activated under specific conditions of ultrasound, is induced to violently rupture near the intended target cell. Rupture of the microbubble releases the incorporated optically active reporter, and also induces poration and active transcelluler transport of the adjacent cell; this process results in delivery of the optically active reporter into the cell or incorporation into the cell membrane.

We also describe herein a method for rapid imaging of multiple molecular markers using optical imaging. Microbubbles carrying an optically active reporter and a targeting ligand are administered to the subject and allowed to accumulate at the target site. After imaging and/or quantification of the accumulated microbubbles by optical imaging and/or ultrasound imaging, the microbubbles within the target tissue are destroyed by the application of ultrasound energy of defined frequency and acoustic pressure. This acoustic treatment results in the slow, non-violent disruption of microbubbles by gas diffusion and deflation, and does not result in delivery of the optically active reporter to the adjacent cells; rather, the optically active reporter is gradually released from the microbubble into the blood stream and cleared via the typical methods. This results in the effective clearance of the contrast agent from the target tissue and re-establishment of the pre-contrast baseline; a second population of microbubbles targeted to a second molecular marker may now be administered and subsequently imaged.

There is limited prior art in the use of gas-encapsulated microparticles, such as microbubbles, in the context of optical imaging. Xu and colleagues (2009) created an air-encapsulated microbubble composed of a PLGA polymer shell, in which the fluorphore indocyanine green was encapsulated. This invention is limited to fluorophores that can be dissolved in the PLGA, and may not be suitable for the wide range of fluorophores described in the current invention. Additionally, the Xu agent requires complex processing, while the lipid agents described here are prepared in a simple two-step process. Finally, Xu does not demonstrate targeted adhesion of the microbubbles, which is crucial to achieving molecular specificity.

Several non-microbubble tracers have been used for near-infrared imaging. For example, Papagiannaros and colleagues (2009) reported using lipid micelles labeled with Alexa-750 for optical imaging of tumors. Unlike the current invention, the micelles described by Papagiannaros do not contain encapsulated gas, and are therefore not expected to be acoustically responsive. Makino and colleagues (2009) created a PLGA nanoparticle with a NIR label. This agent was able to accumulate specifically within tumors and be imaged by optical imaging, although there is no associated gas content and these agents are therefore not acoustically responsive. Xu developed a similar PLGA nanoparticle. This agent is a 200 nm diameter "nanobubble" that contains an optical probe and an antibody targeting ligand. Although Xu and colleagues demonstrated that this agent is acoustically active, acoustically-mediated clearance of this agent at conventional ultrasound frequencies is unlikely due to the very small size of the nanobubble.

The microbubble agents disclosed here are advantageous over existing optically-active contrast agents for several reasons. 1) The described microbubbles can carry a larger payload of optically active probe(s) than previously described contrast agents. 2) The large size of the microbubbles relative to other contrast agents makes the microbubbles purely intravascular tracers, which can cause a reduction in non-specific accumulation of targeted agents. 3). Additionally, the microbubble agents can be effectively cleared from the circulation very rapidly by the application of low-frequency ultrasound energy to the body. This enables repeated administration of microbubbles targeted to different targets within the same patient.

SPECIFIC EXAMPLES

The following examples illustrate, but in way are intended to limit the invention.

Example 1

Synthesis of Microbubbles by Sonication

Microbubbles consisting of a lipid monolayer encapsulating decafluorobutane gas (SynQuest) are prepared by mixing 40 mg of distearoyl phosphatidylcholine (Avanti Polar Lipids) and 20 mg polyoxyethylene-40 stearate (Sigma-Aldrich). This mixture is added to 20 mL of sterile normal saline and sonicated to clarity using a probe-type sonicator. Decafluorobutane gas is dispersed through the aqueous phase via a thin capillary tube, and sonication continued until the formation of microbubbles, sizes of 1-30 um (mean size 1-5 um). The resulting microbubbles are stabilized with a lipid monolayer and augmented with polyoxyethylene as an emulsifier. Microbubbles so prepared are stored refrigerated under a perfluorocarbon atmosphere until further use.

Microbubbles are also prepared with different shell compositions, including denatured proteins, sugars, and non-biological polymers. For example, decafluorobutane microbubbles stabilized by a shell composed of dextrose and albumin are prepared as follows. 30 mL of dextrose is mixed with 10 mL of human serum albumin by low-intensity sonication. Decafluorobutane gas is then dispersed through the mixture, and microbubbles are formed by high-power sonication at the gas/liquid interface.

Example 2

Synthesis of Microbubbles with Reactive Groups

Microbubbles bearing the reactive group 2-pyridyl disulfide (PDP), to which targeting ligands or optically active probes may be immobilized, are prepared as follows. Microbubbles consisting of a lipid monolayer encapsulating decafluorobutane are prepared by mixing 40 mg of phosphatidylcholine, 20 mg polyoxyethylene 40 stearate, and 5 mg of PDP-PEG(2000)-disteroylphosphatidylethanolamine (Avanti). This mixture is added to 20 mL of sterile normal saline (Baxter) and sonicated to clarity using a probe-type sonicator. Decafluorobutane gas is dispersed through the aqueous phase via a thin capillary tubing and sonication continued with the formation of microbubbles, sizes of 1-30 um (mean size 1-5 um). The resulting microbubbles are stabilized with a lipid monolayer and augmented with a polyoxyethylene brush for improved stability and PDP residues on a long polymer tether for the subsequent ligand conjugation. Microbubble material is stored refrigerated in sealed glass vials with a perfluorocarbon atmosphere until further use.

Various other ligand conjugation chemistries can be readily utilized by substituting for the DSPE-PEG(2000)-PDP component. For example, microbubbles bearing biotin (suitable for binding a biotinylated ligand via an avidin-based linker) are be prepared by the inclusion of 5 mg/mL biotin-PEG(2000)-DSPE. Alternatively, ligands can be immobilized via thioether linkage by incorporating 5 mg/mL of maleimide-PEG(2000)-DSPE. Other entities suitable for covalent ligand conjugation are outfitted onto a microbubble surface in a similar manner, including, but not limited to, a hapten, peptide or peptide mimetic, a carbohydrate ligand, a carboxyl, a primary amino group, an active ester grouping, dithiopyridyl residue, or vinyl ether. A schematic of the targeted microbubble is shown in FIG. 2.

Example 3

Synthesis of Microbubbles with Near Infrared Fluorescent Probe within Shell

Figure 4:
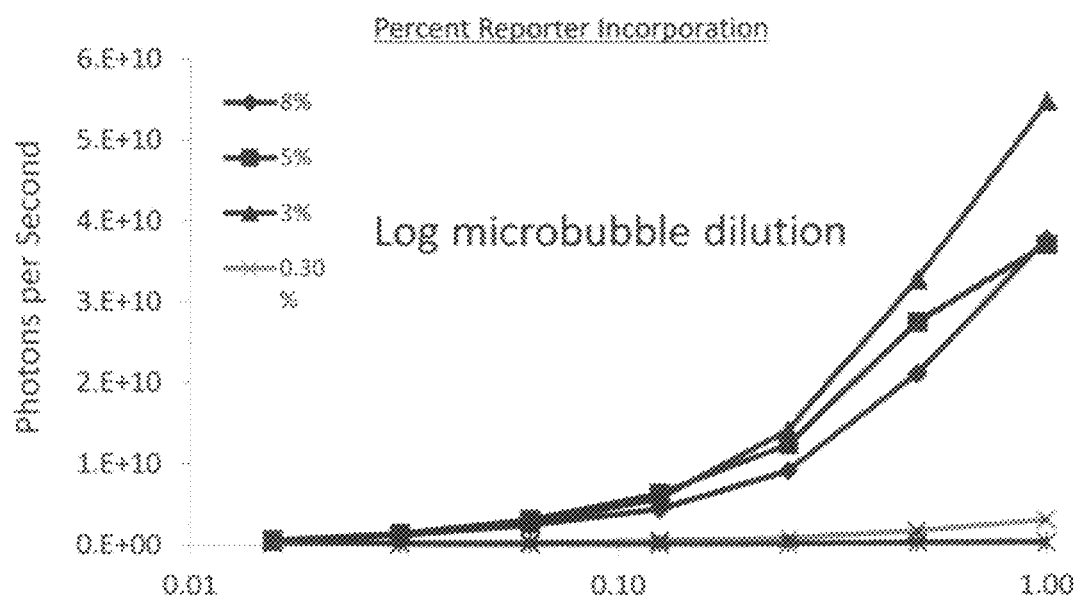
FIG. 4 illustrates the validation loading of microbubbles with the lipophilic fluorophore DiR. Microbubbles were prepared as in Example 3. The fluorophore composed between 0 to 8% of the microbubble shell. Serial dilutions in PBS were performed in a 96 well plate, and the plate was imaged in a Xenogen IVIS at 710/800 nm. Quantified optical signal, measured in photons per second.

Lipid-perfluorocarbon microbubbles containing a near-infrared fluorophore within the shell are prepared as follows. 40 mg of distearoyl phosphatidylcholine, 20 mg of polyoxyethylene-40 stearate, and 2 mg of 1,1-dioctadecyl-3,3,3,3-tetramethylindotricarbocyanine iodide (DiR, 748/780 nm; Invitrogen) are added to 20 mL of normal sterile saline and sonicated using a probe-type sonicator. Decafluorobutane gas is dispersed through the aqueous phase via a capillary tube, and sonication continued with the formation of microbubbles, sizes of 1-30 um (mean size 1-5 um). The resulting microbubbles are stabilized with a lipid monolayer and augmented with polyoxyethylene as an emulsifier. The lipophilic near infrared fluorophore DiR is incorporated into the microbubble shell. Microbubbles so prepared can be stored refrigerated in glass vials containing a perfluorocarbon atmosphere until further use. Several lipophilic dyes known to the art can be used in this invention, including but not limited to carbocyanine dyes and their derivatives. Microbubbles bearing a fluorophore within the shell are demonstrated in FIG. 3 B, wherein the resulting optical signal is measured by fluorescence spectroscopy using a plate reader. The effect of varying the density of the reporter within the shell is demonstrated in FIG. 4, wherein the resulting optical signal is measured using an optical scanner (Xenogen IVIS) at an excitation/emission of 710/800 nm. The optical signal resulting from microbubbles bearing a near infrared probe (DiR) within the shell is shown 5, wherein the resulting optical signal is measured using an optical scanner (Xenogen IVIS) at an excitation/emission of 710/800 nm.

Example 4

Synthesis of Microbubbles with Probe Immobilized on Surface of Shell

Lipid-perfluorocarbon microbubbles bearing a surface-bound PDP are prepared by sonication as in Example 1. The bioluminescent probe luciferase is conjugated to the PDP residues on the surface of the microbubble via disulfide conjugation chemistry, as follows. Luciferase (is dissolved in PBS and incubated with 20-fold excess SPDP for 30 minutes. Unreacted SPDP is removed by gel filtration or dialysis against buffered saline. Conjugation of SPDP to luciferase is verified by the production of pyridine-2-thione upon addition of 10 mM dithiothreitol (DTT), measured by the change in absorbance at 343 nm. The PDP-bearing luciferase is reduced to expose a thiol by treatment with DTT, and 4 nmoles of thiol-luciferase is incubated with 1E9 of PDP-bearing microbubbles for 2 hours under perfluorocarbon.

Optically active probes such as fluorophores can also be conjugated to the microbubble shell using similar method. For example, a cystine-terminated BODIPY molecule (commercially available from Invitrogen) is reduced with equimolar TCEP (Pierce Thermo Fisher), and incubated with PDP-bearing microbubbles at a molar excess of 5:1. Unreacted fluorophore is removed by centrifugal flotation, as described in Example 5. Optimization of fluorophore conjugation is demonstrated in FIG. 3A.

Optically active probes that are active in the near-infrared region are preferred for the applications described herein. For example, the NIR fluorophore IRDye800 (LiCor) was terminated with maleimide. PDP-bearing microbubbles were incubated in 50 mM DTT for 30 minutes, then centrifuged to remove unreacted components (as in Example 5). IRDye800-maleimide was added to PDP-MB at a 5-fold molar excess and incubated for 2 hours under perfluorocarbon. Unreacted fluorophore is removed by flotation, as described in Example 5.

Several suitable NIR fluorophores are commercially available, including carbocyanine dyes, Cyanine dyes (GE Healthcare), DyLight™ dyes (Thermo Scientific), Alexafluor™ dyes (Invitrogen), IRDyes™ (LiCor), and VivoTag™ (Visen). Additional reporters include, but are not limited to, merocyanines, indocyabines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthroquinones, napthoquiones, indathrenes, phthaloylacridones, trisphenoquinones, azo dyes, intramolecular and intermolecular charge transfer dyes and complexes, tropones, tetrazines, bis(dithiolene) complexes, bis(benzene dithiolate) complexes, iodaniline dyes, bis(S,O dithiolene) complexes, and fluorescent proteins and peptides.

Figure 5:
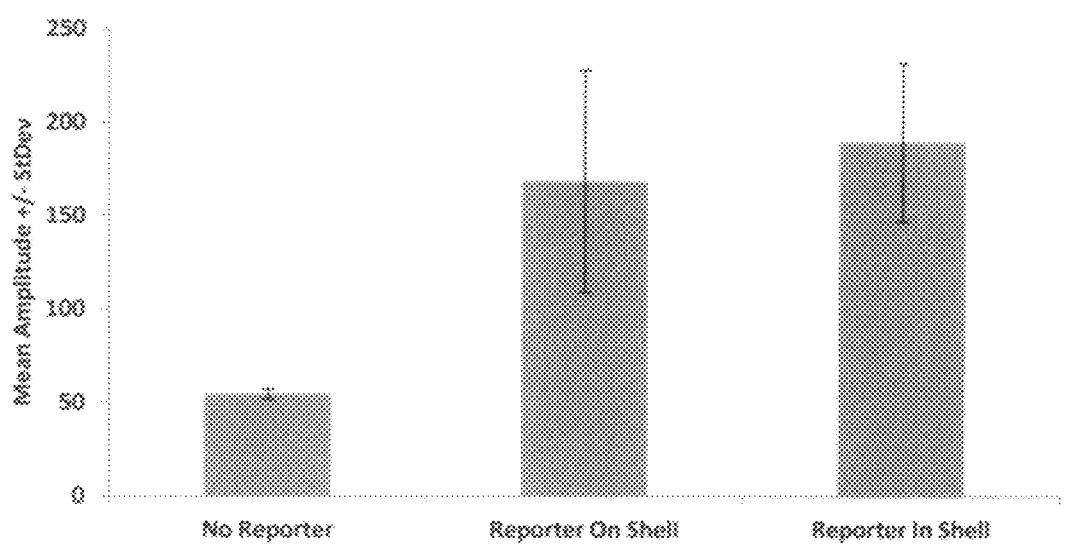
FIG. 5 illustrates optical imaging of microbubbles bearing a NIR probe in vitro. Imaging microbubbles bearing a near-infrared probe using a commercially-available optical imaging scanner (IVIS, from Xenogen). A 100 uL droplet containing ~1E8 microbubbles was placed on the surface of a plastic petri dish. The optical signal resulting from the microbubbles was read in photons/s using a Xenogen IVIS, with filters for 710/800 nm. The optical signal was quantified by drawing a region of interest around the droplet containing contrast agents and measuring the mean pixel amplitude and standard deviation within the region of interest. As a negative control, microbubbles without any fluorophore were prepared, as in Example 1 (No Reporter, shown in first column). As an example of immobilizing a reporter on the surface of the microbubble, the near infrared probe IRDye 800 (Li-Cor) was immobilized on the shell (as in Example 4), shown in the second column. As an example of immobilizing the reporter within the shell, the lipophilic reporter DiR (Invitrogen) was used (as in Example 3), shown in the right column.

Conjugation of a fluorophore to the surface of the microbubble shell is demonstrated in FIG. 3A. The optical signal resulting from microbubbles bearing a near infrared probe (IRDye 800) conjugated to the surface of the shell is shown in FIG. 5.

Example 5

Removal of Unincorporated Reactants by Flotation

Further treatment of the microbubbles synthesized as in Specific Example 2, 3 or 4 may be performed to remove probe, ligand, fluorophore, reactant byproducts, or shell components not incorporated into the microbubble. The microbubble dispersion is diluted to 10 mL in sterile normal saline which has been degassed to less than 1% dissolved oxygen and subsequently saturated by vigorous shaking with decafluorobutane gas. The diluted microbubbles are placed in a sealed glass vial, the headspace of which contains greater than 95% perfluorocarbon gas, and refrigerated with the vial upright for 6 hours. Microbubbles form a cake at the top of the dispersion, and the infranatant, containing unincorporated substances (emulsifier, lipid, fluorophore), is removed by suction through a 1 mm diameter capillary tube. The procedure is repeated once, resulting in a relatively clear infranatant substantially free of unincorporated substances. Subsequent rounds of flotation may be used for generation of preparations of increased purity. Flotation by centrifugation is also possible. For example, microbubbles are diluted as described above, and the dispersion is placed in a 50 mL glass screw-cap bottle, the headspace of which contains decafluorobutane. The bottles are centrifuged at 400XG for 5 minutes, resulting in a cake of microbubbles; infranatant can be removed by suction. This procedure can be repeated to obtain a microbubble dispersion of desired purity from unincorporated components.

Example 6

Clustering of Lipophilic Near Infrared Fluorophores within Microbubble Shell

Lipophilic fluorophores partition into the expanded phase of the lipid microbubble shell, while lipids form a close-packed condensed phase. The fraction of the shell that contains expanded phase substances can be controlled by the rate at which microbubbles prepared by sonication are cooled. By controlling the cooling rate, the surface density of the fluorophores can be controlled to induce, for example, clustering of fluorophores within expanded domains of the shell.

Example 7

Conjugation of Ligands to Microbubbles

Covalent conjugation of ligands to PDP bearing microbubbles is achieved via disulfide bonding. The PDP structure contains a disulfide bond, which enables a rapid interchange reaction with available sulfhydryl moieties on a ligand. A single-chain VEGF ligand (scVEGF), which binds to VEGF receptors up-regulated in angiogenic tumors, is used as a model ligand for this example (SibTech). A terminal sulfhydryl on the scVEGF ligand is exposed by incubating 3.9E-18 moles of scVEGF for 30 min with equimolar DTT in Tris-HCl buffer (100 mM, pH 8.0). The reduced scVEGF is then incubated with PDP microbubbles prepared as in Specific Example 2 at a concentration of 2.5E9 per mL in 1.0 mL of perfluorocarbon saturated sterile saline. The microbubble/ligand dispersion is sealed in a 3 mL glass reaction vial containing a headspace of >95% perfluorocarbon gas. The microbubble preparation is gently agitated on a rocker at room temperature for two hours. Reaction by-products are removed by three rounds of centrifugal flotation as described in Specific Example 8.

Other ligands, such as monoclonal antibodies, can be readily conjugated to the microbubble surface. For example, a rat-anti-mouse P-selectin monoclonal antibody (clone Rb40.34; Pharmingen) was reacted with 30 fold excess SPDP for 30 minutes, then purified by gel exclusion chromatography. The SPDP-antibody was then reacted with 10 mM DTT for 30 minutes to expose a sulfhydryl group, followed by purification by gel exclusion chromatography. The antibody was then reacted with DiR-containing maleimide-terminated microbubbles (prepared as in Example 2) at a 5-fold molar excess for 2 hours. Unreacted ligand was removed as in Example 8. Conjugation of a scVEGF ligand to the surface of maleimide or PDP-bearing microbubbles is demonstrated in FIG. 6.

Example 8

Removal of Unreacted Ligand

Unreacted ligand not bound to microbubble surfaces are removed by centrifugal washing. Microbubble/ligand dispersions are placed in 5 ml syringes from which the plunger had been removed, diluted to 5 ml with sterile perfluorocarbon saturated saline, and centrifuged for 4 minutes at 400×G using a bucket centrifuge. After centrifugation microbubbles form a cake at the top of the syringe, and the infranatant is drained from the syringe through a luer-lock stopcock. This procedure is repeated 4 times to remove the majority of unreacted ligand from the microbubble dispersions.

Example 9

Quantification of Ligand Conjugated to Microbubble Surfaces

The extent of scVEGF ligand conjugation to microbubbles prepared in Specific Example 7 is quantified with an enzyme-linked immunosorbent assay to human VEGF (Invitrogen). Alternatively, quantification of ligands on the microbubble surface may be performed by flow cytometry with a fluorescently labeled secondary antibody, or by radioimmunoassay with a radiolabelled secondary antibody. Microbubble concentration is determined by electrozone sensing using a Coulter II Multisizer. Microbubbles are subsequently disrupted by bath sonication or positive pressurization. The products are then incubated in the ELISA microplate wells with immobilized monoclonal antibodies that bind scVEGF. The plate is subsequently washed, and bound ligand is detected with an HRP-conjugated secondary. Following washing, a colorimetric detection solution is added to the microplate, and the optical density of the resulting solution at 450 nm is measured with a microplate reader. The optical density is linearly related to the concentration of scVEGF over 4 decades, and a standard curve is used to obtain the concentration of scVEGF in the microbubble samples. scVEGF microbubbles prepared as in Specific Example 8 exhibit approximately 1.42E5 molecules/microbubble.

Example 10

Functional Adhesion of Targeted Microbubbles

Figure 7:
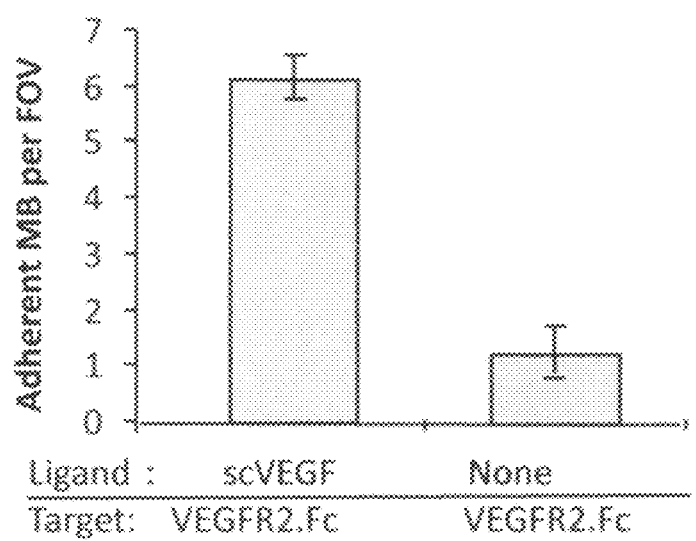
FIG. 7 Illustrates targeted adhesion of microbubbles to a molecular marker of angiogenesis in vitro. Adhesion of microbubbles bearing scVEGF as a targeting ligand to recombinant human VEGF receptor 2 (VEGFR2.Fc) or the non-specific blocker protein casein as assessed in an inverted flow chamber, as in Example 10. Statistically significant increase in adhesion is seen for microbubbles bearing the scVEGF ligand than for control microbubbles.

The functionality of scVEGF microbubbles prepared as in Specific Example 7 is verified in an in vitro adhesion assay. 35 mm polystyrene culture dishes are washed with methanol, and incubated with 200 ng recombinant human VEGFR2 (R&D Systems) overnight at 4 degrees C. Dishes are subsequently washed three times with 0.05% TWEEN-20 and incubated for 1 hour at room temperature with casein to block non-specific adhesion. As a negative control, some dishes are incubated with casein alone (no VEGFR2). Dishes are assembled into an inverted parallel plate flow chamber. Microbubbles bearing scVEGF or no ligand are diluted to 2.5E6 MB/mL in degassed, perfluorocarbon saturated saline and infused through the flow chamber at a shear stress of 1.0 dyne/cm$^2$ using a withdrawal syringe pump. Microbubble adhesion to the dish surface is observed from above using an upright microscope, and microscopic data are recorded using a digital video camera. Adherent microbubbles within 20 fields of view are counted after 5 minutes of infusion. Microbubbles bearing scVEGF exhibit 5-10 fold greater adhesion relative to non-targeted microbubbles on VEGFR2, or to scVEGF microbubbles on casein alone. Specific adhesion of targeted microbubbles is demonstrated in FIG. 7.

Example 11

Use of Microbubbles for Ultrasound Imaging

The microbubbles described in Examples 1-7 are used for ultrasound imaging as follows. Microbubbles are injected intravenously at a dose of 1E7 into an anesthetized mouse bearing an experimental tumor. An ultrasound transducer is clamped over the tumor, and a field of view encompassing the tumor and adjacent tissue is obtained. The entry of the microbubbles into the tumor vasculature is visualized using a microbubble imaging mode (such as pulse-inversion, harmonic, sub-harmonic, and the like) over 5-25 minutes.

Microbubbles within the animal are cleared by insonating the tumor and other tissues under specific acoustic conditions of moderate acoustic power (10-500 kPa) at a low pulsing frequency (<1 Hz) for several cycles. This ultrasound energy is applied by a diagnostic ultrasound scanner, a single-element transducer, a therapeutic ultrasound device, a sonoporator, or similar device. The mechanism of microbubble destruction under the conditions described above is outward-directed diffusion of the encapsulated gas. Each pulse of ultrasound causes an oscillation of the microbubble and escape of a portion of the encapsulated gas through the shell into the surrounding milleu. Subsequent pulses further diminish the gas content of the microbubble, leading to collapse. After clearance of microbubbles, a subsequent microbubble dose is administered and imaged as above; this process is repeated for several microbubble formulations targeted to various molecular targets or tissues.

Example 12

Use of Microbubbles for Biolumenescence Imaging

The microbubbles described in Examples 3-7 are used for bioluminescence imaging as follows. Microbubbles bearing luciferase immobilized on the surface are injected intravenously at a dose of 1E7 into an anesthetized mouse bearing an experimental tumor. The mouse is injected intraperitoneally with 100 ug of luciferin 1-25 minutes after microbubble administration. The bioluminescence produced by the oxidation of luciferin by luciferase is imaged using a optical imaging scanner capable of detecting bioluminescence. The optical imaging procedure is described in U.S. Pat. No. 5,650,135, herein incorporated by reference.

Microbubbles within the animal are cleared by insonating the tumor and other tissues under specific acoustic conditions of moderate acoustic power (~200 kPa) at a low pulsing frequency (<1 Hz) for several cycles. This ultrasound energy is applied by a diagnostic ultrasound scanner, a single-element transducer, a therapeutic ultrasound device, a sonoporator, or similar device. The mechanism of microbubble destruction under the conditions described above is outward-directed diffusion of the encapsulated gas. Each pulse of ultrasound causes an oscillation of the microbubble and escape of a portion of the encapsulated gas through the shell into the surrounding milieu. Subsequent pulses further diminish the gas content of the microbubble, leading to collapse. The microbubble remnants are allowed to clear by the usual biological pathways over 5-25 minutes. After clearance of microbubbles, a subsequent dose is administered and imaged as above; this process is repeated for several microbubble formulations targeted to various molecular targets.

Example 13

Use of Microbubbles for Near Infrared Imaging

The microbubbles described in Examples 2-7 are used for near infrared imaging as follows. Microbubbles bearing a near infrared probe immobilized on or within the microbubble are injected intravenously at a dose of 1E7 into an anesthetized mouse bearing an experimental tumor. The light emitted by the fluorescent probe is detected and quantified using an optical imaging scanner capable of detecting near infrared emissions.

Figure 8:
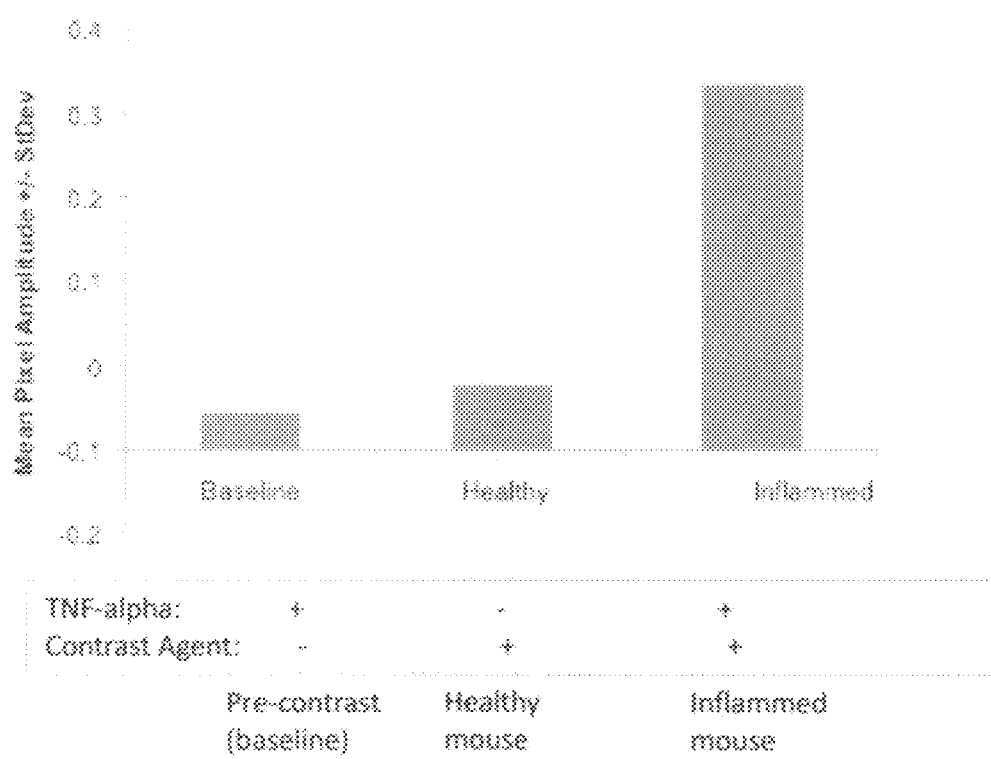
FIG. 8 illustrates the accumulation and in vivo imaging of targeted MB bearing a NIR reporter, as in Example 13. Microbubbles bearing a P-selectin antibody as a targeting ligand, and containing 3% DiR were administered to healthy mice, or mice that had been pre-administered 500 ng of TNF-alpha to the left hindleg. Significant accumulation was observed within the inflamed (TNF-alpha treated) hindlimb relative to control tissues (healthy mouse) or mice in which no microbubbles were administered (pre-contrast baseline).

For example, as shown in FIG. 8 microbubbles containing 3% DiR and bearing biotin reactive groups were derivatized with streptavidin, then with a biotinylated anti-P-selectin antibody (clone Rb40.34; Pharmingen). The targeted microbubbles were then administered intravenously by retroorbital injection at a dose of 1E8 microbubbles in 100 uL to an anesthetized mouse that had been pre-administered 500 ng of TNF-alpha to the left hindleg 1 hour before the experiment. TNF-alpha causes a localized inflammatory response, characterized by up-regulation of P-selectin. As a negative control, microbubbles were administered to an untreated (healthy) mouse. Animals were imaged in a Xenogen IVIS at 710/800 nm before microbubble administration (pre-contrast baseline) and two minutes after administration. Significant accumulation of microbubbles within the inflamed hindleg was observed in the TNF-alpha treated mouse. A diffuse and low-amplitude signal was observed in the healthy mouse, and only within the vicinity of the liver. Data was quantified (shown in FIG. 8) by drawing a region of interest around the left hindlimb, a separate region around the right hindlimb, and computing the mean pixel amplitude within each region. The difference between the two regions was computed, and normalized by the untreated (right) region. The quotient represents the increase in signal in the treated (left) hindlimb relative to the untreated (right) hindlimb.

Example 14

Acoustically-Mediated Clearance of Microbubbles

Figure 9:
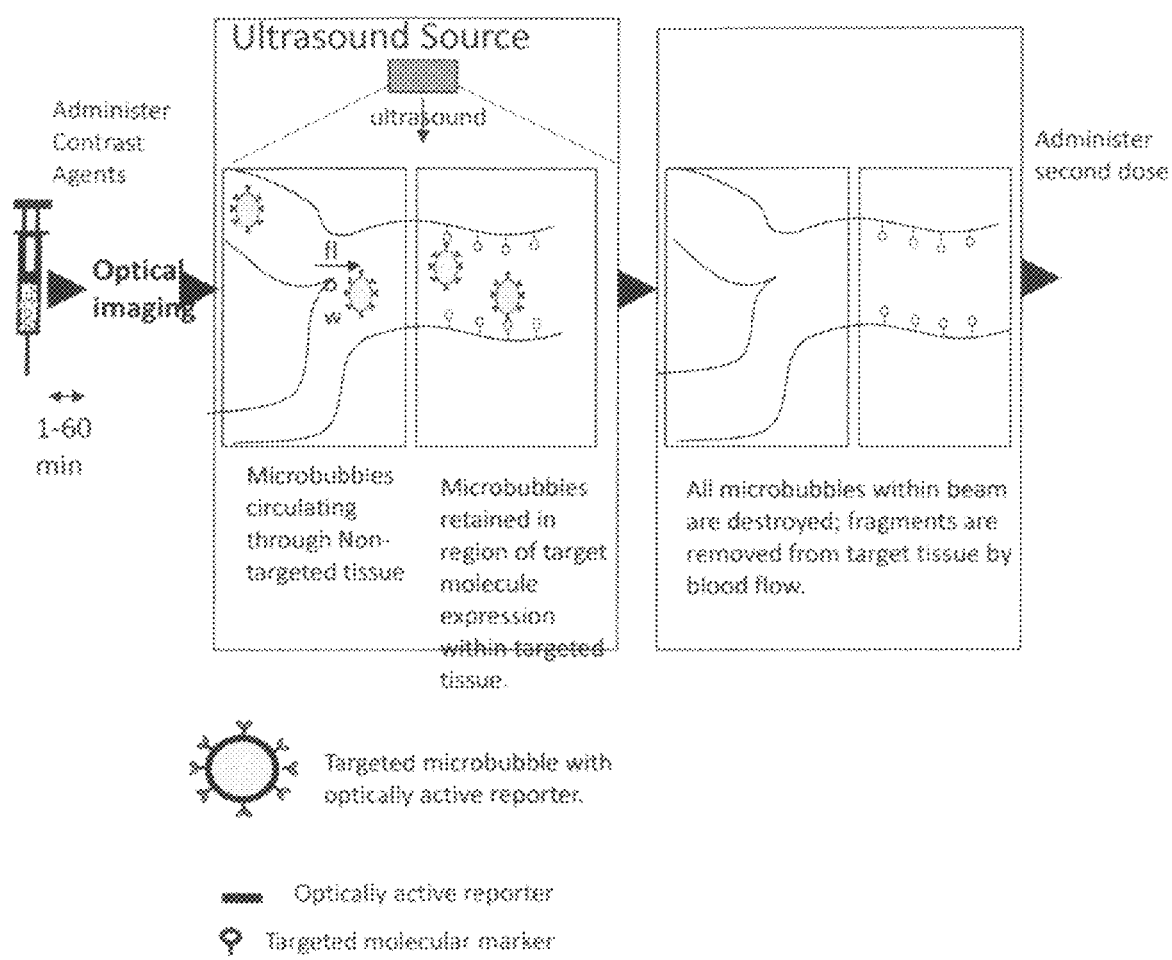
FIG. 9 illustrates a schematic demonstrating the concept of acoustically-mediated microbubble clearance, as described in Example 14.

Microbubbles within the animal can cleared by insonating the tissues under specific acoustic conditions, as shown in FIG. 9. Specifically, low frequency (0.5-10 MHz) moderate acoustic power (10-500 kPa) at a low pulsing frequency (0.1-1000 Hz) for several cycles is desired. This ultrasound energy is applied by a diagnostic ultrasound scanner, a single-element transducer, a therapeutic ultrasound device, a sonoporator, or similar device. The mechanism of microbubble destruction under the conditions described above is outward-directed diffusion of the encapsulated gas. Each pulse of ultrasound causes an oscillation of the microbubble and escape of a portion of the encapsulated gas through the shell into the surrounding milieu. Subsequent pulses further diminish the gas content of the microbubble, leading to collapse. The microbubble remnants are allowed to clear by the usual biological pathways over 1-25 minutes. After clearance of microbubbles, a subsequent dose is administered and imaged as above; this process is repeated for several microbubble formulations targeted to various molecular targets.

For example, microbubbles bearing the near-infrared fluorophore DiR within the shell were prepared as in Example 3. The microbubbles were diluted to approximately $10^5$ per mL in normal saline, and placed into an acoustically-permeable Opticell cartridge (Nunc). The cartridge was imaged with the Xenogen IVIS, as in Example 13. The cartridge was then insonated using a hand-held transducer operating at 1.0 MHz, and power density of 2 W/cm$^2$ (peak negative pressure of 300 kPa). The Opticell cartridge was then imaged as above. A significant decrease in optical signal was observed, and quantified as in FIG. 10.

For example, microbubbles targeted to P-selectin were administered to a TNF-alpha stimulated mouse as in Example 13. After confirming accumulation of microbubbles at the target site (left hindleg), the mouse was treated with ultrasound delivered by a hand-held transducer operating at 1.0 MHz, at a peak negative pressure of 300 kPa. The ultrasound probe was immobilized over the abdomen and legs of the animal. Following two minutes of insonation, the mouse was imaged with the optical imaging scanner as in Example 13. The mouse was then re-scanned to determine whether microbubble signal remained within the hindleg. No detectible signal remained within the targeted hindleg, and a diffuse signal, corresponding to cleared optically-active shell remnants, was observed in the region of the liver.

Figure 11:
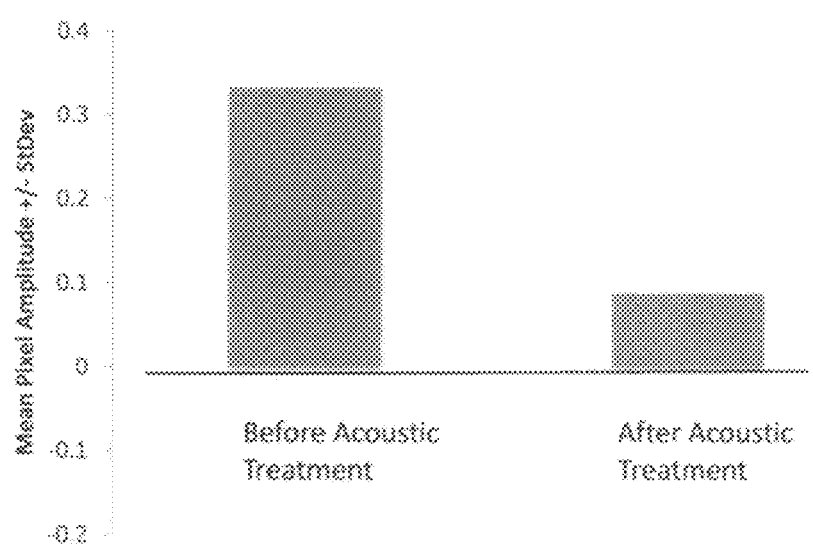
FIG. 11 illustrates a demonstration of acoustically-mediated microbubble clearance in vivo, as described in Example 14. Microbubbles bearing a P-selectin antibody as a targeting ligand, and containing 3% DiR were administered to mice that had been pre-administered 500 ng of TNF-alpha to the left hindleg. After imaging accumulated microbubbles, the hindlimb was exposed to ultrasound energy (300 kPa, 1.0 MHz) to destroy the microbubbles. The mouse was then re-scanned to determine whether microbubble signal remained within the hindleg. A significant reduction in signal was observed after acoustic treatment.

Data was quantified (shown in FIG. 11) by drawing a region of interest around the left hindlimb, a separate region around the right hindlimb, and computing the mean pixel amplitude within each region. The difference between the two regions was computed, and normalized by the untreated (right) region. The quotient represents the increase in signal in the treated (left) hindlimb relative to the untreated (right)) hindlimb. A significant reduction in signal was observed after acoustic treatment.

Example 15

Therapeutic Use of Optically Active Microbubbles

Microbubbles bearing an optically active probe are used for therapeutic means, for example to disrupt tumor vasculature, as follows. Microbubbles bearing an optically active probe immobilized on or within the shell, in addition to a photosensitizing agent, are targeted to angiogenic tumor cells by inclusion of a VEGFR2 ligand as described in Example 7. Numerous photosensitizers known to the art can be used in this embodiment, including photofrin, synthetic diporphyrins and dichlorins, phthalocyanines, chloroaluminium phthalocyanine, verdins, purpurins, etiopurpurin, hydroporphyrins, bacteriochlorins, chlorins, and other benzoporphyrin derivatives. Microbubbles are administered intravascularly to the patient, and allowed to accumulate within the tumor over 1-30 minutes. The specific accumulation of microbubbles can be observed by ultrasound or optical imaging. Tumor-bound microbubbles are then ruptured using a brief, high-pressure ultrasound pulse focused on the target site, and the target is immediately treated with the appropriate wavelength to mediate the tumorocidal effects of the photosensitizer.

What is claimed is:

1. An injectable microbubble optical imaging contrast agent composition comprising a gas core encapsulated by a monolayer shell, said shell consisting of two shell-forming surfactants, a first shell-forming surfactant and a second shell-forming surfactant having a higher water solubility than said first shell-forming surfactant, an anchor molecule attached to said shell at the gas-shell interface and an optically-active probe, said probe being detectable by fluorescence, near-infrared, bioluminescence, or other optical imaging methods and incorporated into the shell of the microbubble, immobilized on the surface of the shell, or attached to the microbubble shell on the distal tip of a polymer tether, wherein said probe emits light over one or more wavelengths between 200-1000 nm, wherein said first shell-forming surfactant is present in the shell in a moles/moles ratio of 50-75%, relative to other shell components, wherein said second shell-forming surfactant is present in the shell in a moles/moles ratio of 15-50%, relative to other shell components and wherein said probe is present in the shell in a moles/moles ratio of 0.1-10%, relative to other shell components.

2. The composition of claim 1 further comprising a targeting ligand attached to said anchor molecule.

3. The composition of claim 1 wherein said first shell-forming surfactant is a phospholipid or mixture of phospholipids having at least one acyl chain having between 10 and 28 carbon atoms.

4. The composition of claim 1 wherein said first shell-forming surfactant is a phosphatidylcholine.

5. The composition of claim 1 wherein said second shell-forming surfactant is selected from the group consisting of: fatty acids and salts thereof, sugar esters of fatty acids, PEG-phospholipids, PEG-stearate, DSPE-PEG-2000, DSPE-PEG-350, or DSPE-PEG-1000.

6. The composition of claim 1 wherein said optically active probe is selected from the group consisting of carbocyanine dyes and their derivatives, merocyanines, indocyanines, phthalocyanines, naphalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthroquinones, napthoquiones, indathrenes, phthaloylacridones, trisphenoquinones, azo dyes, intramolecular and intermolecular charge transfer dyes and complexes, tropones, tetrazines, bis(dithiolene) complexes, bis(benzene dithiolate) complexes, iodaniline dyes, bis(S,O dithiolene) complexes.

7. The composition of claim 1 wherein said optically active probe is selected from the group consisting of fluorescent proteins of the GFP and RFP family, fluorescent peptides, light emitting proteins from the luciferase family, and photosensitizers.

8. The composition of claim 6 wherein said optically active probe is 1,1-dioctadecyl-3,3,3,3-tetramethylindotricarbocyanine, or a salt thereof.

9. The composition of claim 2 wherein said targeting ligand is a hormone, amino acid, peptide, peptidomimetic, protein, nucleic acid, deoxyribonucleic acid, ribonucleic acid, lipid, antibody, receptor molecule, carbohydrate, aptamer, or combination thereof.

10. The composition of claim 2 wherein said targeting ligand is an antibody that binds specifically to molecules found on the vascular endothelial surface, whose presence is correlated with increased inflammation or angiogenesis.

11. The composition of claim 2 wherein said targeting ligand is a peptide or protein that binds specifically to molecules found on the vascular endothelial surface, whose presence is correlated with increased inflammation or angiogenesis.

12. The composition of claim 1 wherein said gas core is selected from group consisting of air, nitrogen, argon, sulfur hexafluoride, perfluoroethane, perfluoropropanes, perfluorobutanes, perfluorocyclobutanes, perfluoropentanes, perfluorocyclopentanes, perfluoro methylcyclobutanes, perfluorohexanes, perfluorocyclohexanes, perfluoro methyl cyclopentanes, perfluoro dimethyl cyclopentanes, perfluoro heptanes, perfluoro cycloheptanes, perfluoro cycloheptanes, perfluoromethyl cyclohexanes, perfluoro dimethyl cyclopentanes, perfluoro trimethyl cyclobutanes perfluoro triethylaminesperfluoropropane, perfluorobutane and similar, or a mixture thereof.

13. The composition of claim 1 wherein said targeting ligand is present in the shell in a moles/moles ratio of 0.1-5%, relative to other shell components.

14. The composition of claim 1 wherein said anchor molecule is selected from the group consisting of lipids, phospholipids, long-chain aliphatic hydrocarbons, lipid multi-chains, comb-shaped lipid polymer steroids, fullerenes, polyaminoacids, native or denatured proteins, aromatic hydrocarbons, fatty acids, or partially or completely fluorinated lipids.

15. The composition of claim 14 wherein said anchor is a phosphatidylethanolamine-PEG.

16. A method of optical imaging a living subject comprising:
  a. administering to a subject the composition of claim 1 in a physiologically acceptable carrier;
  b. allowing sufficient time for said composition to accumulate at a target site in the subject,
  c. imaging the subject using an optical imaging scanner able to detect light emitted from said composition at one or more timepoints.

17. A method of optical imaging a living subject comprising:
  a. administering to the subject the composition of claim 1 in a physiologically acceptable carrier,
  b. allowing sufficient time for said composition to accumulate at a target site,
  c. imaging the subject using an optical imaging scanner able to detect light emitted from said composition at one or more timepoints,
  d. applying acoustic energy at the target site of the subject in order to rupture the microbubbles and effectively clear them from the target location,
  e. administering into the subject a second composition of claim 1 in a physiologically acceptable carrier,
  f. allowing sufficient time for said second composition to accumulate at a target site, g. imaging the subject using an optical imaging scanner able to detect light emitted from said composition at one or more timepoints.

18. The method of claim 17 wherein steps (d) through (g) are repeated at least one time.

19. The method of claim 17 wherein the time allowed for the composition to accumulate at the target site is between 1-60 minutes.

20. The method of claim 17 wherein imaging the subject further comprises optically exciting said contrast agent composition in vivo by illuminating the subject with light of wavelength between 200-1000 nm, and subsequently detecting the emitted light from the contrast agent.

21. The method of claim 17 wherein said acoustic energy is defined by a combination of center frequency and acoustic pressure, and wherein the center frequency is between 0.1-10 MHz, and the acoustic pressure is between 0.05-10 MPa.

22. The method of claim 17 wherein said living subject is a mouse.

23. The method of claim 17 wherein said living subject is a human.

24. The method of claim 17 wherein said composition is administered to the subject by intravenous, retro-orbital, subcutaneous, intraperitoneal, intra-lymphatic intravascular, oral, intramuscular, intraperitoneal, intralymphatic.subcutaneous, intranasal, intrarectal, interstitial, topically, or intratumoral injection, bolus or infusion.

* * * * *